(12) United States Patent
Hesse et al.

(10) Patent No.: US 6,291,392 B2
(45) Date of Patent: *Sep. 18, 2001

(54) CATALYSTS CONTAINING A PLATINUM GROUP METAL AND PRODUCED IN A SOL-GEL METHOD, AS WELL AS A METHOD FOR PRODUCING DIARYLCARBONATES

(75) Inventors: Carsten Hesse, Tönisvorst; Ulrich Notheis, Dormagen; Johann Rechner, Kempen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,591

(22) PCT Filed: Aug. 5, 1998

(86) PCT No.: PCT/EP98/04862

§ 371 Date: Feb. 11, 2000

§ 102(e) Date: Feb. 11, 2000

(87) PCT Pub. No.: WO99/08787

PCT Pub. Date: Feb. 25, 1999

(30) Foreign Application Priority Data

Aug. 18, 1997 (DE) .............................. 197 35 770

(51) Int. Cl.⁷ .............................. B01J 21/06; B01J 23/32; C07C 69/96
(52) U.S. Cl. .............................. 502/234; 502/324; 558/274
(58) Field of Search .............................. 502/234, 324; 558/274

(56) References Cited

U.S. PATENT DOCUMENTS

| | | | |
|---|---|---|---|
| 3,887,494 | 6/1975 | Dietz | 252/452 |
| 3,900,457 | 8/1975 | Witt | 260/94.9 D |
| 4,152,503 | 5/1979 | Short et al. | 526/106 |
| 4,169,926 | 10/1979 | McDaniel | 526/106 |
| 4,436,883 | 3/1984 | Witt | 526/106 |
| 5,336,803 | 8/1994 | Kezuka et al. | 558/277 |
| 5,380,907 | 1/1995 | Mizukami et al. | 558/270 |
| 5,750,459 | * 5/1998 | Marella et al. | 502/304 |
| 6,001,768 | 12/1999 | Buysch et al. | 502/230 |

FOREIGN PATENT DOCUMENTS

| | | |
|---|---|---|
| 28 15 512 | 10/1979 | (DE) . |
| 0177198 | * 4/1985 | (EP) . |
| 0736325 | * 4/1995 | (EP) . |
| 4-261142 | 9/1972 | (JP) . |
| 1-165551 | 6/1989 | (JP) . |
| 4-257546 | 9/1992 | (JP) . |

OTHER PUBLICATIONS

Mat. Res. Soc. Symp. Proc., 21 (month unavailable) 1988, pp. 81–92, Ram C. Mehrotra, "Polymetallic Alkoxides—Precursor For Ceramics".

Chem. Rev. 90 (month unavailable) 1990 p. 969, K. G. Caulton et al "Synthesis, Structural Principles, and Reactivity of Heterometallic Alkoxides".

J. Catal. 161 (month unavailable) 1996, pp. 651–658, D.C.M. Dutoit et al "Titania—Silica Mixed Oxides".

* cited by examiner

Primary Examiner—Jane C. Oswecki
(74) Attorney, Agent, or Firm—Joseph C. Gil; James R. Franks

(57) ABSTRACT

Described is a process for preparing an aromatic carbonate, e.g., diphenyhl carbonate, in which an aromatic hydroxy compound, e.g., phenol, is reacted with carbon monoxide and oxygen in the resence of a supported catalst prepared by a sol-gel process, a quatermary ammonium or phosphonium salt and a base. The sol-gel supported catlyst comprises: (i) a first metal oxide selected from the group consisting of silicon oxide, aluminum oxide, titanium oxide, zirconium oxide and mixtures thereof; (ii) a second metal oxide selected from the group consisting of oxides of the elements of groups 4, 5, 6, 7, 11, 12, 13, 14, the iron group (atomic numbers 26 to 28), the rare-earth metals (atomic numbers 58 to 71) and mixtures thereof; and (iii) a metal selected from the group consisting of platinum metals, compounds of platinum metals (atomic numbers 44 to 46 and 77 and 78) and mixtures thereof. The sol-gel supported catlyst is aged, dried and optionally annealed prior to use in the process of the present invention.

12 Claims, No Drawings

CATALYSTS CONTAINING A PLATINUM GROUP METAL AND PRODUCED IN A SOL-GEL METHOD, AS WELL AS A METHOD FOR PRODUCING DIARYLCARBONATES

This application is a 371 of PCT/EP98/04862 filed Aug. 5, 1998.

The present invention relates to platinum metal-containing mixed oxide catalysts which have been prepared in a sol-gel process and their use in a process for preparing diaryl carbonates by reacting aromatic hydroxy compounds with carbon monoxide and oxygen.

It is known that organic carbonates can be prepared by oxidative reaction of aromatic hydroxy compounds with carbon monoxide in the presence of a noble metal catalyst (DE-OS 28 15 512). Palladium is preferably used as the noble metal. In addition a co-catalyst (e.g. manganese or cobalt salts), a base, a quaternary salt, a variety of quinones or hydroquinones and a drying agent may also be used. The procedure may be performed in a solvent, preferably in methylene chloride.

In order to perform this process in an economic manner, effective recovery of the noble metal catalyst is a critical factor, in addition to the activity and selectivity of the catalyst. On the one hand the noble metal catalyst represents a large cost factor. Losses of noble metal catalyst have to be replaced at great cost. On the other hand no residues of the noble metal catalyst should remain in the product. The economic and efficient recovery of homogeneous catalysts for the process of oxidative carbonylation of aromatic hydroxy compounds to give diaryl carbonates has not hitherto been described. The separation of a noble metal catalyst from a liquid reaction mixture, e.g. by filtering or centrifuging, can be performed at low cost if heterogeneous supported catalysts are used.

In EP-A 572 980, EP-A 503 581 and EP-A 614 876 noble metal supported catalysts are used which contain 5% palladium on carbon supports. However, these types of supported catalysts produce only very unsatisfactory conversions or even none at all, so that these are also unsuitable for an economically viable process.

JP-A 01/165 551 (cited in accordance with C.A. 112:76618j (1990)) describes using palladium or palladium compounds such as palladium acetylacetonate, in combination with alkali metal or alkaline earth metal iodides or 'onium' iodides, such as tetrabutylammonium iodide, and at least one zeolite to prepare aromatic carbonates.

JP-A 04/257 546 and JP-A 04/261 142 each describe an example of a supported catalyst for preparing aromatic carbonates in which silicon carbide granules are used as the support material for a supported catalyst in a distillation column. Although drastic conditions (high pressure, high temperature) are used in the relevant examples, these catalysts produce only very low space-time yields. These low space-time yields make the economic production of aromatic carbonates with this type of supported catalyst impossible.

EP-A 736 324 describes the preparation of diaryl carbonates with heterogeneous catalysts which contain a platinum metal, preferably palladium, and a co-catalytic metal compound, preferably a metal from the group Mn, Cu, Co, Ce and Mo. When preparing the catalysts the co-catalytic metals are applied to a support.

EP-A 736 325 describes the preparation of diaryl carbonates with heterogeneous catalysts which contain a platinum metal, preferably palladium, on a support which consists of a metal oxide in which the metal may exist in several valency states.

Although these supported catalysts enable the preparation of aromatic carbonates for the first time, a further increase in activity is desirable from an economic point of view.

It has now been found that higher catalyst activities can be obtained if mixed oxides e.g. of V, Mn, Ti, Cu, La, the rare-earth metals and mixtures thereof which have been prepared in a sol-gel process and which contain platinum metals are used a catalysts.

The invention provides catalysts which contain
(i) an oxide of the elements silicon, aluminium, titanium, zirconium or a mixture of oxides of these elements,
(ii) one or more co-catalytic metal oxides from groups 4, 5, 6, 7, 11, 12, 13, 14, the iron group (atomic numbers 26 to 28) or the rare-earth metals (atomic numbers 58 to 71) in the periodic system of the elements in accordance with the new IUPAC nomenclature, and
(iii) one or more platinum metals or one or more compounds of platinum metals (atomic numbers 44 to 46 and 77 and 78) in an amount 0.01 to 15 wt. %, calculated as platinum metal and with respect to the total weight of catalyst,
which are obtained by preparing a gel from one or more suitable precursor(s) of the components mentioned under (i) and (ii) and the platinum metal component (iii), ageing, drying and optionally annealing the gel.

The gel according to the invention can be prepared by almost any known method. Methods which are known for preparing mixed oxides based on a gel are preferably used. This includes, for example, the hydrolysis of one or more metal alkoxides and/or hydrolysable metal compounds under acid, neutral or basic conditions in suitable solvents at temperatures of 0° C. to 200° C. In this case mixtures of different precursors of one or more elements may also be used.

Suitable precursors of silicon dioxide are alkoxides of silicon such as, for example, tetraethoxysilane, tetramethoxysilane.

Suitable precursors of aluminium oxide are lower alkoxides such as trimethoxyaluminium, triethoxyaluminium, tri-n-propoxyaluminium, tri-iso-propoxyaluminium, tri-sec-butoxyaluminium, tri-sec-butoxyaluminium, or tri-tert-butoxyaluminium or aluminium alkoxides with chelating ligands such as dibutoxyaluminium-ethylacetoacetate.

Suitable precursors of titanium oxide are tetramethoxytitanium, tetraethoxytitanium, tetraisopropoxytitanium; suitable precursors of zirconium oxide are tetraethoxyzirconium, tetra-tert-butoxyzirconium, tetra-n-butoxyzirconium, tetra-iso-propoxyzirconium. Suitable hydrolysable salts are for example titanium tetrachloride, organic salts such as aluminium acetylacetonate, zirconium acetylacetonate or the corresponding mixed metal compounds and salts.

Suitable solvents are, for example, monohydric alcohols such as methanol, ethanol, n-propanol, iso-propanol, n-butanol, 2-butanol, t-butanol, polyhydric alcohols such as glycol, 1,2-propanediol, 1,3-propanediol, monofunctional or polyfunctional ketones such as acetone, 1,3-pentanedione (acetylacetone), cyclic or linear ethers with one to three oxygen atoms such as tetrahydrofuran, dioxan, diethyl ether, glycoldiethyl ether or diethyleneglycoldiethyl ether, ether-alcohols such as glycolmonomethyl ether, nitriles such as acetonitrile and benzonitrile and amides such as dimethylformamide. Alcohols, diketones and ether-alcohols are preferred. Obviously mixtures of solvents may also be used.

The solvents are used in amounts such that the molar ratio of alkoxide to solvent is 1:0.2 to 1:100.

Partially alkylated precursors $R^1_x M(OR^2)_y$ may also be used in the process according to the invention, wherein M represents one of the elements mentioned under (i), (x+y) is the valency of the element and $R^1$ and $R^2$, independently of each other, represent alkyl, aralkyl or aryl groups with 1 to 20 carbon atoms. The following may be mentioned by way of example: methyltriethoxysilane, ethyltriethoxysilane.

Co-catalytic compounds which may be mentioned are one or more compounds of elements from the groups 4, 5, 6, 7, 11, 12, 13, 14, the iron group (atomic numbers 26 to 28) or the rare-earth metals (atomic numbers 58 to 71) in the periodic system of elements (IUPAC, new) with a total molar proportion of the components mentioned under (ii) of 0.1% to 99.9%, preferably 0.1% to 40%, in particular 0.5% to 20%, with respect to the total number of moles of the components mentioned under (i) and (ii), introduced into the catalyst, preferably Mn, Cu, Co, V, Nb, W, Zn, Ce, Mo, in particular Mn, Co, Cu, Mo, Ce, quite specifically Mn and/or Ce.

Suitable precursors of the co-catalytic metals are basically known, and the following may be used for example: inorganic salts such as halides, oxides, nitrates, sulphates, carboxylates, salts of monofunctional or polyfunctional organic $C_2$ to $C_{15}$ carboxylic acids such as acetates, cyclohexane butyrates, diketonates such as acetylacetonate, ethyl hexanoate, alkoxides such as methoxides, ethoxides and isopropoxides and complex compounds which contain, for example, carbon monoxide, olefins, amines, nitriles, phosphines and halides, as well as mixed salts.

Heterometallic alkoxides of the formula $[L_m M-(OR)_2-M'L_n']$ are also known and are described, for example, by Mehrotra et al in Mat. Res. Soc. Symp. Proc. 121 (1988) 81; D. C. Bradley et al in "Metal Alkoxides", Academic Press, NY (1978); K. G. Caulton et al in Chem. Rev. 90 (1990) 969.

Examples of compounds containing organic ligands which may be mentioned are: cerium(IV) isopropoxide, cerium(IV) methoxyethoxide, cerium(III) acetylacetonate, cobalt carbonylmethoxide, cobalt(II) acetylacetonate, cobalt (III) acetylacetonate, manganese(II) ethoxide, manganese (II) acetylacetonate, manganese(III) acetylacetonate, copper (II) 2-ethylhexanoate, copper(II) ethoxide, copper(II) ethylacetoacetate, copper(II) acetylacetonate, niobium(V) ethoxide, molybdenum(V) ethoxide(dimolybdenum decaethoxide), molybdenum(VI) oxide-bisacetylacetonate, vanadium(IV) oxide-bisacetylacetonate(vanadyl acetylacetonate), vanadium(III) acetylacetonate, vanadium tri-isopropoxide oxide, vanadium tri-n-propoxide oxide, tungsten(VI) ethoxide, tungsten(V) ethoxide, tungsten(VI) phenoxide, zinc(II) acetylacetonate.

Suitable platinum metal compounds are, for example, the platinum metal compounds and platinum metal-containing complex compounds described in EP-A 736 324. In, the examples mentioned, palladium was mentioned as the platinum metal, but other platinum metals are also suitable such as Pt, Ir, Ru or Rh, Pd and Rh, however, are preferred, in particular Pd. Further examples of suitable platinum metal compounds are: $Li_2(PdCl_4)$, $Na_2(PdCl_4)$, $K_2(PdCl_4)$, $(NBu_4)_2 (PdCl_4)$, $Na_2(PdBr_4)$, $K_2(PdBr_4)$, $(NBu_4)_2(PdBr_4)$ (where Bu=n-butyl), platinum metal nitrates, acetates, propionates, butyrates, oxalates, carbonates, oxides, hydroxides, acetylacetonates and other compounds familiar to a person skilled in the art. Examples of olefin-containing, platinum metal complexes are [allylpalladium chloride] dimer $[C_3H_5 PdCl]_2$, 1,5-cyclooctadienpalladium dichloride $C_8H_5PdCl_2$; examples of phosphine-containing platinum metal complexes are 1,2-bis[(diphenylphosphino)ethane] palladium dichloride $Pd[(C_6H_5)_2PCH_2CH_2P(C_6H_5)_2]Cl_2$, bis(triphenylphosphino)palladium dichloride $Pd[P(C_6H_5)_3]_2 Cl_2$; examples of amine-containing platinum metal complexes are diamminopalladium dibromide $Pd(NH_3)_2Br_2$, diamminopalladium dichloride $Pd(NH_3)_2Cl_2$, tetraamminopalladiumtetrachloropalladate $[Pd(NH_3)_4][PdCl_4]$; examples of nitrile-containing platinum metal complexes are bis(acetonitrile)palladium dichloride $Pd(CH_3CN)_2Cl_2$, bis(benzonitrile)palladium dichloride $Pd(C_6H_5CN)_2Cl_2$; examples of carbon monoxide-containing platinum metal complexes are tetrabutylammonium tribromocarbonylpalladate $(NBu_4)Pd(CO)Br_3$ (where Bu=n-butyl) and tetrabutylammonium trichlorocarbonylpalladate $(NBu_4)Pd(CO)Cl_3$ (where Bu=n-butyl).

Catalysts according to the invention may be prepared in one or more steps. In this case the platinum metal is introduced into the mixture, when preparing the mixed oxide, immediately or some time later. Modes of operation in which some of the amount of platinum metal is introduced into the sol-gel process and the remainder is applied onto the mixed oxide at a later point are also possible.

When preparing catalysts according to the invention, a solution of the precursors of (i) and (ii) are conventionally prepared in a suitable solvent and hydrolysed with 1 to 20, preferably 1.5 to 10 mole equivalents of water, with respect to the total number of moles of compounds (i) and (ii). The water may be added in one or several portions, pure, mixed with other solvents or together with the precursors of (ii) or the platinum metal compounds dissolved therein.

According to the invention, one or more compounds of the platinum metals (atomic numbers 44 to 46 and 77 and 78) may be introduced to the catalyst at different points in time in an amount of 0.01 to 20 wt. %, preferably 0.05 to 10 wt. % calculated as platinum metal and given with respect to the total weight of the final catalyst.

In a preferred variant of the catalyst preparation, one or more platinum metal compounds are added before, during or after gelling to the mixture of precursors of (i), (ii), the solvent, the water and optionally the acids or bases described above as a solution in a suitable solvent.

A soluble compound may be formed in situ from an insoluble precursor of the platinum metal compound by using a complexing agent or a further ligand. In another preferred embodiment, the platinum metal compound is dissolved in the solvent used and added in that form. In a further preferred embodiment, the platinum metal compound is added as solid or solution to the pre-hydrolysed mixture.

During the hydrolysis procedure, acids or bases may be added in amounts of 0.1 to 200 mol. % with respect to the total number of moles of compounds (i) and (ii).

Suitable acids are, for example, hydrochloric acid, nitric acid, sulphuric acid, formic acid, acetic acid or higher carboxylic acids with 3 to 8 carbon atoms. Di- and tricarboxylic acids with up to 8 carbon atoms are also suitable. Suitable bases are ammonia, quaternary ammonium hydroxides, $NR_4OH$, in which the R groups, independently of each other, may be alkyl, aryl or aralkyl groups with 1 to 15 carbon atoms, e.g. tetramethyl-, tetraethyl-, tetrapropyl-, tetrabutyl-, tetrapentyl- or tetraphenylammonium hydroxide, or organic nitrogen bases such as amines, pyridines, guanidines. Preferred bases are ammonia and quaternary ammonium hydroxides. The acids and bases may be used as pure substances, as anhydrous solutions or as aqueous solutions.

When adding the individual components, efficient homogenisation of the mixture should be ensured by using appropriate mixing devices such as e.g. stirrers or mixing nozzles.

If several compounds (i) and (ii) are hydrolysed, known techniques may be applied in order to mutually adjust their reactivities. The following may be mentioned by way of example: pre-hydrolysis of one compound, chemical modification of one compound with a chelating agent, the use of different alkoxide groups in the compounds and hydrolysis at different temperatures, such as is described, for example, by D. A. Ward and E. I. Ko (Ind. Eng. Chem. Res. 34 (1995) 421).

Another suitable method for preparing mixtures according to the invention from precursors of (i) and (ii) is the gelling of inorganic precursors in aqueous systems, such as the preparation of silica gels by neutralising alkali metal silicates with strong acids. Additional steps, such as washing the gel, may be required in order to wash salts which have been formed out of the mixture. During the procedure described here the precursor of (ii) or the platinum metal-containing compounds (iii) may be added, for example, to one of the components before mixing the alkali metal silicate and acid.

After gelling, it is advantageous to allow the gels to age at temperatures of 20 to 100° C., preferably 20 to 80° C., for a period of at least 10 minutes. The upper limit to the ageing time is restricted only by economic factors and may be several weeks. Times between one hour and two weeks are preferred. Ageing may also be performed in several steps at different temperatures or at a temperature which changes slowly with time.

The gels are dried after they have been aged. Drying the gels may be performed by a variety of methods, depending on the method of preparation, wherein drying has an effect on the internal surface area and the pore volume of the materials.

Drying may take place on the one hand in air, under a vacuum or in a stream of gas. Suitable gases for drying the gel in a gas stream are nitrogen, oxygen, carbon dioxide or noble gases or any mixture of the gases mentioned, preferably e.g. air. Gaseous hydrocarbons for example alkanes such as methane, ethane, propane, butane, alkenes such as ethene, propene, butene, butadiene and alkynes such as ethyne, propyne, etc in any composition may also be used. Drying is performed at 0 to 300° C., preferably 20 to 250° C., in particular at 20 to 150° C. The drying time depends e.g. on the porosity of the gel and on the solvent used. It is generally a few hours, for example 0.5 to 50 h, preferably 1 to 40 h, in particular 1 to 30 h.

Another preferred method is drying under supercritical conditions such as, for example, is described by G. M. Pajonk (Applied Catalysis 72 (1991) 217) and Dutoit et al (J. Catal. 161 (1996) 651), and this leads to gels with particularly high porosities. Carbon dioxide ($T_{critical}=31°$ C., $P_{critical}=73$ bar) or alcohols above their critical point (e.g. for ethanol $T_{critical}=243°$ C., $P_{critical}=63$ bar), for example, may be used. Drying may be performed, batchwise, continuously or part-continuously, optionally in the presence of another inert gas.

Reduction of the platinum metal may occasionally occur during supercritical drying with alcohols and this generally has a negative effect on the activity of the catalysts according to the invention. In these cases it is recommended that the catalysts be oxidised again after drying, for example by annealing at 200 to 800° C. in a stream of gas which contains oxygen, air, halogens or hydrogen halides.

Further methods of drying, particularly for gels prepared in aqueous systems, are extractive and azeotropic drying such as are described, for example, in U.S. Pat. Nos. 3,887,494, 3,900,457, 4,169,926, 4,152,503, 4,436,883, 4,081,407.

After drying the dried mixed oxides may be calcined. Calcining may take place in air, under vacuum or in a gas stream. Suitable gases for calcining mixed oxides in a gas stream are e.g. nitrogen, oxygen, carbon dioxide or noble gases and any mixtures of the gases mentioned, preferably air. Calcining is performed at 100 to 800° C., preferably at 100 to 700° C., in particular at 100 to 600° C. It may sometimes be of advantage if the composition of the gas is altered either suddenly or continuously during calcination. The calcining time is generally a few hours, for example 0.5 to 50 h, preferably 1 to 40 h, in particular 1 to 30 h.

It is also possible to apply the mixed oxides according to the invention as a layer on other catalyst supports. Suitable support materials for the application of a layer of metal mixed oxide are any industrially conventional catalyst supports based on carbon, oxides of elements, carbides of elements or salts of elements in a variety of forms. Examples of carbon-containing supports are coke, graphite, carbon black or active carbon. Examples of elemental oxide catalyst supports are $SiO_2$ (natural or synthetic silicas, quartz), $Al_2O_3$ in a variety of modifications ($\alpha, \gamma, \delta, \eta, \theta$), aluminas, natural and synthetic aluminosilicates (zeolites), $TiO_2$ (rutile, anatase), $ZrO_2$ or ZnO. Examples of elemental carbides and salts are SiC, $AlPO_4$, $BaSO_4$, $CaCO_3$, etc. They may be used either as chemically uniform pure substances or as mixtures. Powdered or particulate materials, or even monoliths, are suitable for use according to the invention.

The invention also provides a process for preparing an organic carbonate by reacting an aromatic hydroxy compound with carbon monoxide and oxygen in the presence of the catalysts according to the invention, a quaternary ammonium or phosphonium salt and a base.

The organic carbonate prepared by the process according to the invention corresponds to the formula $$R\text{—}O\text{—}CO\text{—}O\text{—}R \quad (I)$$

in which

R represents a substituted or non-substituted $C_6$–$C_{12}$ aryl group, preferably a substituted or non-substituted phenyl group, in particular a non-substituted phenyl group.

Aromatic hydroxy compounds which may be used according to the invention correspond to the formula $$R\text{—}O\text{—}H \quad (II)$$

in which R is defined as above. Aromatic hydroxy compounds which can be reacted using the supported catalysts according to the invention are for example phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol or bisphenol-A, preferably phenol. The aromatic hydroxy compound may be substituted with one or two substituents such as a $C_1$–$C_4$ alkyl group, a $C_1$–$C_4$ alkoxy group, fluorine, chlorine or bromine.

Catalysts according to the invention may be used as powders, moulded items or monoliths, preferably as powders or moulded items, and are separated from the reaction mixture by e.g. filtration, sedimentation or centrifuging.

Preparation of aromatic carbonates using supported catalysts according to the invention may be performed in a variety of ways. One possibility is a batchwise process. In the event of a continuous mode of operation in either a counter-flow or parallel flow system, or in the trickle phase on a fixed bed catalyst, loads of 0.01 to 20 g of aromatic hydroxy compound per gram of supported catalyst per hour, preferably 0.05 to 10 g of aromatic hydroxy compound per gram of supported catalyst per hour, in particular 0.1 to 5 g of aromatic hydroxy compound per gram of supported catalyst per hour are used. The supported catalyst used in batchwise trials may be used repeatedly with the same feed materials without any purification. With a continuous mode of operation the supported catalysts used may remain in the reactor for a long time. A continuous mode of operation in a single reactor or in a cascade of reactors are preferably used when using supported catalysts according to the invention.

If the supported catalyst is used as a powder, the stirred container to be used for mixing the reaction components is fitted with stirrers which can be used for this purpose. When working with supported catalyst powders as a suspension in stirred vessels or bubble columns, amounts of 0.001 to 50 wt. %, preferably 0.01 to 20 wt. %, in particular 0.1 to 10 wt. % of supported catalyst powder, with respect to the amount of aromatic hydroxy compound used, are used. In particularly preferred embodiments, the heterogeneous supported catalyst is used as moulded items fixed in place in stirred tanks, bubble columns, trickle phase reactors or cascades of these reactors, wherein different types of reactors may also be used in combination in a cascade.

In the event that the catalyst is arranged as a fixed bed, the catalyst is preferably used as moulded items, e.g. as spheres, cylinders, small rods, hollow cylinders, rings, etc. If required, catalysts may be modified further by extruding, making tablets, optionally adding further catalyst supports or binders such as $SiO_2$ or $Al_2O_3$, and calcining. The preparation and further processing of catalysts used according to the invention are generally known to a person skilled in the art and are part of the prior art.

In the process according to the invention any organic or inorganic bases or mixtures of these may be used. Examples of inorganic bases which may be mentioned, without restricting the process according to the invention, are alkali metal hydroxides and carbonates, carboxylates or other salts of weak acids and alkali metal salts of aromatic hydroxy compounds of the formula (II), e.g. alkali metal phenolates. Obviously the hydrates of alkali metal phenolates may also be used in the process according to the invention. An example of this type of hydrate which may be mentioned here, without restricting the process according to the invention, is sodium phenolate trihydrate. The amount of added water, however, is preferably such that a maximum of 5 moles of water are used per mole of base. Higher amounts of water lead, inter alia, to poorer conversions and decomposition of the carbonates being formed. Examples of organic bases which may be mentioned, without restricting the process according to the invention, are tertiary amines which may have $C_6$–$C_{10}$ aryl, $C_7$–$C_{12}$ aralkyl and/or $C_1$–$C_{20}$ alkyl groups as organic groups, or pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6,-pentamethylpiperidine. An alkali metal salt of an aromatic hydroxy compound is preferably used as the base, in particular an alkali metal salt of the aromatic hydroxy compound which is also being reacted to give the organic carbonate. This alkali metal salt may be a lithium, sodium, potassium, rubidium or caesium salt. Lithium, sodium and potassium phenolate are preferably used, in particular sodium phenolate.

The base may be added to the reaction mixture as the pure compound in solid form or as molten material. In a further embodiment of the invention the base is added to the reaction mixture as a solution which contains 0.1 to 80 wt. %, preferably 0.5 to 65 wt. %, in particular 1 to 50 wt. % of the base. Solvents which may be used for this are either alcohols or phenols such as e.g. the phenol participating in the reaction or also inert solvents. Examples are those mentioned below for use as reaction media. These solvents may be used individually or in any combination with each other. Thus there is one embodiment of the process according to the invention, for example, in which the base is dissolved in a molten phenol which has been diluted with a solvent. The base is preferably dissolved in a molten aromatic hydroxy compound, in particular in the molten aromatic hydroxy compound which is intended to be reacted to give the organic carbonate. Quite specifically the base is dissolved in phenol. The base is added in an amount which does not depend on the stoichiometry. The ratio of platinum metal, e.g. palladium, to base is preferably chosen so that 0.1 to 500, preferably 0.3 to 200, in particular 0.9 to 130 equivalents of base, with respect to platinum metal, e.g. palladium, are used per mole of platinum metal, e.g. palladium.

The process according to the invention is preferably performed without using a solvent. Obviously inert solvents may also be used. Examples of solvents which may be mentioned are dimethylacetamide, N-methylpyrrolidinone, dioxan, t-butanol, cumyl alcohol, isoamyl alcohol, tetramethylurea, diethyleneglycol, halogenated hydrocarbons (e.g. chlorobenzene or dichlorobenzene) and ethers.

The quaternary salts used in the context of the present invention may be, for example, ammonium or phosphonium salts substituted with organic groups. Compounds suitable for use in the process according to the invention are ammonium and phosphonium salts which contain, as organic groups, $C_6$–$C_{10}$ aryl, $C_7$–$C_{12}$ aralkyl and/or $C_1$–$C_{20}$ alkyl groups and, as anion, a halide, tetrafluoroborate or hexafluorophosphate. Ammonium salts which are preferably used in the process according to the invention contain, as organic groups, $C_6$–$C_{10}$ aryl, $C_7$–$C_{12}$ aralkyl and/or $C_1$–$C_{20}$ alkyl groups and, as anion, a halide, in particular tetrabutylammonium bromide. The amount of this type of quaternary salt is 0.1 to 50 wt. %, with respect to the weight of the reaction mixture. This amount is preferably 0.5 to 15 wt. %, in particular 1 to 5 wt. %.

The process according to the invention, preferably without a solvent, is performed at 30 to 200° C., preferably 30 to 150° C., in particular 40 to 120° C. at a pressure of 1 to 100 bar, preferably 2 to 50 bar, in particular 5 to 25 bar.

Examples

Comparison Example 1

In Accordance With EP-A 736 324

Preparing a Powdered Manganese Oxide Support 85 g of sodium hydroxide (2.125 mol) dissolved in 200 ml of water were added dropwise to a solution of 126 g of manganese(II) chloride (1 mol) in 500 ml of water. The precipitate obtained in this way was filtered under suction, washed and dried. Then it was annealed for 3 h at 300° C. and for 2 h at 500° C.

Coating the Powdered Manganese Oxide with Palladium 300 ml of a solution of 50 g of sodium tetrachloropalladate(II) hydrate containing 15% palladium in water were added to a slurry of 292.5 g of manganese dioxide powder in 1500 ml of water at room temperature. The mixture was adjusted to be alkaline using dilute caustic soda. The suspension was filtered under suction and dried at 100° C. The heterogeneous catalyst contained 2.5% palladium on an $MnO_2$ support, calculated as metal.

Use of the Supported Catalyst to Prepare Diphenyl Carbonate 8.31 g of tetrabutylammonium bromide and 0.77 g of manganese(II) acetylacetonate dissolved in 450 g of phenol were introduced into an autoclave (1 litre) with a gas dispersion stirrer and condenser and with a cold trap connected in series. Then 4 g of the supported catalyst described above and 2.21 g of sodium phenolate dissolved in 50 g of phenol were added. The pressure was then adjusted to 14 bars bet introducing a gaseous mixture of carbon monoxide and oxygen (95:5 vol. %). The amount of gaseous mixture was adjusted to 350 Nl/h. A sample was withdrawn from the reaction mixture each hour and analysed gas chromatographically. The analyses showed that after 1 h 9.9% of diphenyl carbonate, after 2 h 15.2% of diphenyl carbonate and after 3 h 18.2% of diphenyl carbonate were present in the reaction mixture. 11.8 g of a phenol/water mixture had condensed in the cold trap.

Comparison Example 2

In Accordance with EP-A 736 325

Coating a Powdered Titanium Oioxide with Palladium and Manganese 300 ml of a solution of 40.5 g (0.16 mol) of manganese(II) nitrate tetrahydrate in water were added to a slurry of 283.5 g of titanium dioxide powder (Norton) in 1500 ml of water at room temperature. The mixture was then made alkaline with dilute caustic soda solution. The suspension was filtered under suction, washed with water, dried at 100° C. and annealed for 3 h at 300° C. The support, doped with manganese, was slurried in 1500 ml of water and then 300 ml of solution containing 50 g of sodium tetrachloropalladate(II) hydrate containing 15% of palladium were added. The mixture was adjusted to be alkaline with dilute caustic soda solution. The suspension was filtered under suction, washed and dried at 100° C.

The catalyst contained 2.5% palladium and 3% manganese, each calculated as the metal.

Use of the Supported Catalyst to Prepare Diphenyl Carbonate

The supported catalyst was used to prepare diphenyl carbonate in the same way as described in comparison example 1. The analysis showed that after 1 h 9.6% of diphenyl carbonate, after 2 h 16.1% diphenyl carbonate and after 3 h 21.0% diphenyl carbonate were present in the reaction mixture. 12.3 g of phenol/water mixture had condensed in the cold trap.

Example 1

Preparing a Si/Mn/Pd Co-gel 100 ml of tetraethoxysilane were mixed with a solution of 6.9 g of manganese(III) acetylacetonate and 1.24 g of palladium(II) acetylacetonate in 200 ml of ethanol and then 36 ml of 25.7% strength aqueous hydrochloric acid were added over the course of 18 minutes with stirring. The mixture was allowed to stand for 6 days at room temperature and then dried for 2 days at 40° C. in a vacuum drying cabinet. The solid obtained in this way was milled and annealed for 3 h at 300° C. in a stream of air.

The catalyst contained 1.5% palladium and 3.0% manganese, each calculated as the metal.

Use of the Supported Catalyst to Prepare Diphenyl Carbonate

The supported catalyst was used to prepare diphenyl carbonate in the same way as described in comparison example 1, but with the difference that 6.7 g of catalyst were used. Analysis showed that after 1 h 9.2% diphenyl carbonate, after 2 h 17.8% diphenyl carbonate and after 3 h 24.4% diphenyl carbonate were present in the reaction mixture. 15.0 g of a phenol/water mixture had condensed in the cold trap.

Example 2

Preparing a Si/Mn/Pd Co-gel

The catalyst was prepared in the same way as described in example 1 with the difference that 13.8 g of manganese (III) acetylacetonate, 2.48 g of palladium(II) acetylacetonate and 300 ml of ethanol were used.

The catalyst contained 3.0% palladium and 6.0% manganese, each calculated as the metal.

Use of the Supported Catalyst to Prepare Diphenyl Carbonate

The supported catalyst was used to prepare diphenyl carbonate in the same way as described in example 1, but with the difference that 3.3 g of catalyst were used. Analysis showed that after 1 h 11.6% diphenyl carbonate, after 2 h 21.4% diphenyl carbonate and after 3 h 27.0% diphenyl carbonate were present in the reaction mixture. 16.5 g of a phenol/water mixture had condensed in the cold trap.

Example 3

Preparing a Si/Mn/Pd Co-gel 100 ml of tetraethoxysilane were mixed with a solution of 6.9 g of manganese(III) acetylacetonate in 200 ml of ethanol and then a solution of 1.24 g of potassium tetrachloropalladate in 36 ml of 25.7% strength aqueous hydrochloric acid were added over the course of 18 minutes with stirring. The mixture was allowed to stand at 40° C. for 3 days and then dried for 2 days at 40° C. in a vacuum drying cabinet. The solid obtained in this way was milled and annealed for 3 h at 300° C. in a stream of air.

The catalyst contained 1.5% palladium and 6% manganese, each calculated as the metal.

Use of the Supported Catalyst to Prepare Diphenyl Carbonate

The supported catalyst was used to prepare diphenyl carbonate in the same way as described in example 1. Analysis showed that after 1 h 11.4% diphenyl carbonate, after 2 h 19.2% diphenyl carbonate and after 3 h 24.2% diphenyl carbonate were present in the reaction mixture. 13.9 g of a phenol/water mixture had condensed in the cold trap.

Example 4

Preparing a Si/Mn/Pd Co-gel

The catalyst was prepared as described in example 1 except that a mixture of 17 ml of glacial acetic acid and 30 ml of water were used for hydrolysis instead of hydrochloric acid.

The catalyst contained 1.5% palladium and 6% manganese, each calculated as the metal.

Use of the Supported Catalyst to Prepare Diphenyl Carbonate

The supported catalyst was used to prepare diphenyl carbonate in the same way as described in example 1. Analysis showed that after 1 h 13.4% diphenyl carbonate, after 2 h 19.6% diphenyl carbonate and after 3 h 24.6% diphenyl carbonate were present in the reaction mixture. 15.1 g of a phenol/water mixture had condensed in the cold trap.

What is claimed is:

1. A process for preparing an organic carbonate comprising:
   (I) preparing a catalyst by a process comprising:
   (a) providing a sol-gel comprising,
      (i) a first metal oxide selected from the group consisting of silicon oxide, aluminum oxide, titanium oxide, zirconium oxide and mixtures thereof,
      (ii) a second metal oxide selected from the group consisting of metal oxides of the elements of groups 4, 5, 6, 7, 11, 12, 13, 14, the iron group (atomic numbers 26 to 28), the rare-earth metals (atomic numbers 58 to 71) and mixtures thereof, and
      (iii) a metal selected from the group consisting of platinum metals, compounds of platinum metals (atomic numbers 44 to 46 and 77 and 78) and mixtures thereof, said metal being present in an amount of 0.01 to 15 wt. %, calculated as platinum metal with respect to the total weight of said catalyst, said first metal oxide (i), said second metal oxide (ii) and said metal (iii) each being formed independently from suitable precursors,
   (b) aging said sol-gel to obtain an aged sol-gel; and
   (c) drying said aged sol-gel to obtain said catalyst; and
   (II) reacting an aromatic hydroxy compound with carbon monoxide and oxygen in the presence of said catalyst, a quaternary ammonium or phosphonium salt and a base.

2. The process of claim 1 wherein the catalyst obtained in step (c) is then annealed.

3. The process of claim 1 wherein said second metal oxide (ii) is selected from the group consisting of oxides of the elements manganese, copper, cobalt, vanadium, niobium, tungsten, zing, cerium and mixtures thereof.

4. The process of claim 1 wherein the platinum metal of said metal (iii) is selected from the group consisting of platinum, palladium, iridium, ruthenium, rhodium and mixtures thereof.

5. The process of claim 1 wherein the platinum metal compound of said metal (iii) is selected from the group consisting of $Li_2(PdCl_4)$, $Na_2(PdCl_4)$, $K_2(PdCl_4)$, $(n\text{-butyl})_2(PdCl_4)$, $Na_2(PdBr_4)$, $K_2(PdBr_4)$, allylpalladium chloride dimer, 1,5-cyclooctadienpalladium dichloride, 1,2-bis((diphenylphosphino)ethane)palladium, bis(triphenylphosphino)palladium, diamminopalladium dibromide, diamminopalladium dichloride, tetraamminopalladiumtetrachloropalladate, bis(acetonitrile)palladium dichloride, bis(benzonitrile)palladium dichloride, tetrabutylammonium tribromocarbonylpalladate, tetrabutylammonium trichlorocarbonylpalladate and mixtures thereof.

6. The process of claim 1 wherein said first metal oxide (i) is silicon dioxide; said second metal oxide (ii) is manganese oxide; and said metal (iii) is selected from palladium metal and compounds of palladium metal.

7. The process of claim 1 wherein said base is an inorganic base selected from the group consisting of alkali metal hydroxides and alkali metal salts of aromatic hydroxy compounds.

8. The process of claim 1 wherein said base is an organic base selected from the group consisting of: tertiary amines having organic groups selected from $C_6$–$C_{10}$ aryl, $C_7$–$C_{12}$ aralkyl, $C_1$–$C_{20}$ alkyl and combinations thereof; pyridine bases; and hydrogenated pyridine bases.

9. The process of claim 8 wherein said organic base is selected from the group consisting of triethylamine, tripropylamine, tributylamine, trioctylamine, benzyldimethylamine, dioctylbenzylamine, dimethylphenethylamine, 1-dimethylamino-2-phenylpropane, pyridine and N-methylpiperidine, 1,2,3,6,6-pentamethylpiperidine.

10. The process of claim 1 wherein said quaternary ammonium salt and said quaternary phosphonium salt each independently have: organic groups selected from $C_6$–$C_{10}$ aryl, $C_7$–$C_{12}$ aralkyl, $C_1$–$C_{20}$ alkyl and combinations thereof; and anion groups selected from halide, tetrafluoroborate and hexafluorophosphate.

11. The process of claim 1 wherein said organic carbonate is represented by the following formula,

R—O—C(O)—O—R wherein R is a substituted or non-substituted $C_6$–$C_{12}$ aryl group, and said aromatic hydroxy compound is represented by the following formula,

R—OH wherein R is as described above.

12. The process of claim 11 wherein said aromatic hydroxy compound is selected from the group consisting of m-cresol, p-cresol, o-chlorophenol, phenol, m-chlorophenol, p-chlorophenol, o-ethylphenol, m-ethylphenol, p-ethylphenol, o-propylphenol, m-propylphenol, p-propylphenol, o-methoxyphenol, m-methoxyphenol, p-methoxyphenol, 2,6-dimethylphenol, 2,4-dimethylphenol, 3,4-dimethylphenol, 1-naphthol, 2-naphthol, 4,4'-isopropylidenediphenol and mixtures thereof.

* * * * *